US008105809B2

(12) United States Patent
Henderson

(10) Patent No.: US 8,105,809 B2
(45) Date of Patent: Jan. 31, 2012

(54) ENZYMATIC SYNTHESIS OF ACETOACETATE ESTERS AND DERIVATIVES

(75) Inventor: Samuel T. Henderson, Broomfield, CO (US)

(73) Assignee: Accera, Inc., Broomfield, CO (US)

(*) Notice: Subject to any disclaimer, the term of this patent is extended or adjusted under 35 U.S.C. 154(b) by 576 days.

(21) Appl. No.: 12/167,840

(22) Filed: Jul. 3, 2008

(65) Prior Publication Data
US 2010/0003730 A1 Jan. 7, 2010

(51) Int. Cl.
C12P 7/62 (2006.01)
C07C 69/72 (2006.01)

(52) U.S. Cl. ........................................ 435/135; 560/178
(58) Field of Classification Search .................. 435/135; 560/178
See application file for complete search history.

(56) References Cited

U.S. PATENT DOCUMENTS

| 2,766,145 | A | 10/1956 | O'Brien |
| 2,766,146 | A | 10/1956 | Gilbert |
| 3,053,677 | A | 9/1962 | Touey |
| 4,407,821 | A | 10/1983 | Mendy |
| 4,528,197 | A | 7/1985 | Blackburn |
| 4,551,523 | A | 11/1985 | Elam |
| 4,701,443 | A | 10/1987 | Nelson et al. |
| 4,847,296 | A | 7/1989 | Babayan et al. |
| 4,973,489 | A | 11/1990 | Meyer et al. |
| 5,093,044 | A | 3/1992 | Wretlind et al. |
| 5,126,373 | A | 6/1992 | Brunengraber et al. |
| 5,308,832 | A | 5/1994 | Garleb et al. |
| 5,385,915 | A | 1/1995 | Buxbaum et al. |
| 5,391,375 | A | 2/1995 | Hille et al. |
| 5,420,335 | A | 5/1995 | Birkhahn et al. |
| 5,440,027 | A | 8/1995 | Hasenhuettl |
| 5,451,661 | A | 9/1995 | Wan |
| 5,461,073 | A | 10/1995 | Katayama |
| 5,504,072 | A | 4/1996 | Schmidt et al. |
| 5,508,167 | A | 4/1996 | Rose's et al. |
| 5,519,161 | A | 5/1996 | Birkhahn et al. |
| 5,538,983 | A | 7/1996 | Buxbaum et al. |
| 5,614,560 | A | 3/1997 | Lipton |
| 5,650,148 | A | 7/1997 | Gage et al. |
| 5,693,850 | A | 12/1997 | Birkhahn et al. |
| 5,716,828 | A | 2/1998 | Rose's et al. |
| 5,817,626 | A | 10/1998 | Findeis et al. |
| 5,854,204 | A | 12/1998 | Findeis et al. |
| 5,854,215 | A | 12/1998 | Findeis et al. |
| 5,925,684 | A | 7/1999 | Schweikert et al. |
| 5,935,781 | A | 8/1999 | Poirier |
| 5,936,078 | A | 8/1999 | Kuga et al. |
| 5,980,939 | A | 11/1999 | Kim et al. |
| 6,027,896 | A | 2/2000 | Roses et al. |
| 6,136,862 | A | 10/2000 | Hiraide et al. |
| 6,207,856 | B1 | 3/2001 | Veech |
| 6,218,167 | B1 | 4/2001 | Allen et al. |
| 6,232,345 | B1 | 5/2001 | Hiraide et al. |
| 6,316,038 | B1 | 11/2001 | Veech |
| 6,323,237 | B1 | 11/2001 | Veech |
| 6,380,244 | B2 | 4/2002 | Martin et al. |
| 6,395,306 | B1 | 5/2002 | Cui et al. |
| RE38,604 | E | 9/2004 | Veech |
| 6,835,750 | B1 | 12/2004 | Henderson |
| 6,884,454 | B2 | 4/2005 | Pimentel |
| 7,001,736 | B1 | 2/2006 | Poirier |
| 7,049,078 | B2 | 5/2006 | Poirier |
| 7,087,649 | B2 | 8/2006 | Barth et al. |
| 7,351,736 | B2 | 4/2008 | Veech |
| 2001/0014696 | A1 | 8/2001 | Veech |
| 2001/0041736 | A1 | 11/2001 | Veech |
| 2002/0006959 | A1 | 1/2002 | Henderson |
| 2002/0103139 | A1 | 8/2002 | Weisspapir et al. |
| 2003/0013765 | A1 | 1/2003 | Veech |
| 2003/0022937 | A1 | 1/2003 | Veech |
| 2003/0059824 | A1 | 3/2003 | Henderson |
| 2004/0052926 | A1 | 3/2004 | Apfelbaum |
| 2004/0058873 | A1 | 3/2004 | Esmond et al. |
| 2004/0060077 | A1 | 3/2004 | Esmond |
| 2004/0171671 | A1 | 9/2004 | Veech |
| 2004/0266872 | A1 | 12/2004 | Veech |
| 2005/0013884 | A1 | 1/2005 | Rennels |
| 2005/0031651 | A1 | 2/2005 | Gervais |
| 2005/0043242 | A1 | 2/2005 | Esmond |
| 2006/0122270 | A1 | 6/2006 | Henderson |
| 2006/0134240 | A1 | 6/2006 | Miljkovic |
| 2006/0280721 | A1 | 12/2006 | Veech et al. |

(Continued)

FOREIGN PATENT DOCUMENTS

AU A-17953/83 8/1983

(Continued)

OTHER PUBLICATIONS

Yadav et al. Lipase catalyzed transesterification of methyl acetoacetate with n-butanol. Journal of Molecular Catalysis B: Enzymatic 32 (2005) 107-113.* Oguntimein et al. Lipase Catalysed Synthesis of Sugar Ester in Organic Solvents. Biotechnology Letters vol. 15 No. 2 (Feb. 1993) pp. 175-180.*
Babayan (1987) Lipids 22:417-20 "Medium Chain Triglycerides and Structured Lipids".
Bach et al. (1982) Amer. J. Clinic. Nutr. 36:950-962 "Medium-chain triglycerides: an update".
Bach (1996) J. Lipid Res. 37:708 "The usefulness of dietary medium-chain triglycerides in body weight control: fact or fancy?"
U.S. Appl. No. 11/021,920, filed Dec. 22, 2004, Henderson.
Beckman and Ames (1998) Physiol Rev. 78:547-81 "The Free Radical Theory of Aging Matures".
Beffert et al. (1998) Brain Research Reviews 27:119-142 "The neurobiology of apolipoproteins and their receptors in the CNS and Alzheimer's disease".

(Continued)

Primary Examiner — Taeyoon Kim
(74) Attorney, Agent, or Firm — Swanson & Bratschun, L.L.C.

(57) ABSTRACT

In one embodiment, the present invention includes a method for the synthesis of an ester derivative of acetoacetate. The method includes providing a first ester of acetoacetate and providing an alcohol. The method further includes combining the first ester of acetoacetate and the alcohol in the presence of an enzyme capable of transesterification in a non-aqueous solvent to form the ester derivative of acetoacetate. The method results in the formation of the ester derivative of acetoacetate, which, in one embodiment, is monoacetoacetin.

5 Claims, No Drawings

U.S. PATENT DOCUMENTS

2008/0287372 A1  11/2008  Henderson

FOREIGN PATENT DOCUMENTS

| AU | 749638 | 6/2002 |
| AU | 767238 | 11/2003 |
| EP | 0 348 664 A2 | 1/1990 |
| EP | 0 348 664 A3 | 1/1990 |
| EP | 0519727 | 12/1992 |
| EP | 0676205 | 10/1995 |
| EP | 0808626 | 11/1997 |
| FR | 2 531 632 A1 | 2/1984 |
| GB | 2368011 | 4/2002 |
| JP | 6-287138 | 6/1994 |
| JP | A-6287 138 | 10/1994 |
| JP | 3486778 | 1/2004 |
| WO | WO 91/15963 | 10/1991 |
| WO | WO 95/09146 | 4/1995 |
| WO | WO 96/14063 | 5/1996 |
| WO | WO 98/41200 | 9/1998 |
| WO | WO 98/41201 | 9/1998 |
| WO | WO 99/33853 | 7/1999 |
| WO | WO 99/51097 | 10/1999 |
| WO | WO 00/15216 | 3/2000 |
| WO | WO 00/61079 | 10/2000 |
| WO | WO 01/82928 | 11/2001 |
| WO | WO 02/18400 | 3/2002 |
| WO | WO 02/053121 | 7/2002 |
| WO | WO 2004/077938 | 9/2004 |
| WO | WO 2004/108740 | 12/2004 |
| WO | WO 2004/108740 A2 | 12/2004 |
| WO | WO 2004/108740 A3 | 12/2004 |
| WO | WO 2008005818 A1 * | 1/2008 |

OTHER PUBLICATIONS

Birkhahn et al. (1977) Amer. J. Clin. Nutr. 30:2078-2082 "Intravenous feeding of the rat with short chain fatty acid esters I. Glycerol monobutyrate".

Birkhahn et al. (1978) Amer. J. Clin. Nutr. 31:436-441 "Intravenous feeding of the rat with short chain fatty acid esters II. Monoacetoacetin".

Birkhahn et al. (1979) J. Nutr. 109:7 1168-1174 "Monoglyceryl Acetoacetate: A Ketone Body-Carbohydrate Substrate for Parenteral Feeding of the Rat".

Birkhahn et al. (1986) J. Nutr. 116: 851-864 "Total Parenteral Feeding of Rats with an Acetoacetate Monoglyceride and Glucose Mixture".

Birkhahn et al. (1997) Nutrition 13:3 213-219 "Potential of the Monoglyceride and Triglyceride of DL-3-Hydroxybutyrate for Parenteral Nutrition: Synthesis and Preliminary Biological Testing in the Rat".

Birkhahn et al. (1997) Brit. J. Nutr. 78:155-172 "Synthesis and intravenous infusion into the rat of glyceryl bisacetoacetate, 1-acetoacetamido-2, 3-propane diol, and partially reduced glucosyl pentaacetoacetate".

Blass et al. (1984) Neurochem Pathol 2:103-14 "Alzheimer's Disease: A Metabolic Systems Degeneration?"

Blass (2001) J. Neurosci Res. 66:851-6 "Brain Metabolism and Brain Disease: Is Metabolic Deficiency the Proximate Cause of Alzheimer Dementia?"

Blazquez et al. (1999) J. Neurochemistry 73:1674-1682 "The AMP-Activated Protein Kinase is Involved in the Regulation of Ketone Body Production by Astrocytes".

Blazquez et al. (1999) J. Neurochemistry 72:1759-1768 "The Stimulation of Ketogenesis by Cannabinoids in Cultured Astrocytes Defines Carnitine Palitoyltransferase I as a New Ceramide-Activated Enzyme".

Blazquez et al. (1998) J. Neurochem. 71:1597-1606 "Role of carnitine palmitoyltransferase I in the control of ketogenesis in primary cultures of rat astrocytes".

Broer et al. (1997) J. Biol. Chem. 272:30096-102 "Comparison of Lactate Transport in Astroglial Cells and Monocarboxylate Transporter 1 (MCT 1) Expressing *Xenopus laevis* Oocytes".

Bruno et al. (1995) Alzheimer Disease and Associated Disorders (Medline No. 96063810) Fall 9(3):128-31 "Acetyl-L-carnitine in Alzheimer disease: a short-term study on CSF neurotransmitters and neuropeptides".

Bullock (2002) Br J Psychiatry 180: 135-9 "New drugs for Alzheimer's disease and other dementias".

Corbo and Scacchi (1999) Ann Hum Genet 63:301-310 "Apolipoprotein E (APOE) allele distribution in the world. Is $APOE*4$ a 'thrifty' allele?"

Cox et al. (1998) J. Of Pediatrics 133(2):247-253 "Reversal of severe hypertrophic cardiomyopathy and excellent neuropsychologic outcome in very-long-chain acyl-coenzyme a dehydrogenase deficiency".

Craft et al. (1996) Neurobiology of Aging 17 (1):123-130 "Memory Improvement Following Induced Hyperinsulinemia in Alzheimer's Disease".

Cruz et al. (2001) J. Biol. Chem. 276:12162-12168 "Glucose and Insulin Stimulate Heparin-releasable Lipoprotein Lipase Activity in Mouse Islets and INS-1 Cells".

Davis et al. (1999) Nature 400:810 "Alois Alzheimer and the amyloid debate".

De Vivo et al. (2002) J. Child Neurol. Dec;17 Suppl 3:3S15-23; discussion 3S24-5 "Glucose transporter 1 deficiency syndrome and other glycolytic defects".

DeVries et al. (1997) Biochemistry 36:5285-5292 "Functional Characterization of Mitochondrial Carnitine Palmitoyltransferases I and II Expressed in the Yeast *Pichia pastoris*".

Dewachter et al. (2002) J Neurosci 22:3445-3453 "Neuronal deficiency of presenilin 1 inhibits amyloid plaque formation and corrects hippocampal long-term potentiation but not a cognitive defect of amyloid precursor protein [V717I] transgenic mice".

Dialog Results (Sep. 22, 2003) Agent for Prevention and/or therapeutics of Alzheimer's disease-contg. Triglyceride of 8-10 carbon fatty acids as active ingredient, Translation of Publication No. 06-287138.

Dias 1990 Metabolism 39:9:887 "Effects of Medium-Chain Triglyceride Feeding on Energy Balance in Adult Human".

Edmond (1992) Can J Physiol Pharmacol 70:S118-129 "Energy metabolism in developing brain cells".

Evans et al. (1989) JAMA 262 (18):2551-2556 "Prevalence of Alzheimer's Disease in a Community Population of Older Persons".

Finch et al. (1997) Experimental Neurology 143:82-102 "Aging, Metabolism, and Alzheimer Disease: Review and Hypotheses".

Frolich et al. (1998) J Neural Transm 105:423-438 "Brain insulin and insulin receptors in aging and sporadic Alzheimer's disease".

Gelman et al. (1999) Cell Mol Life Sci 55(6-7): 932-43 "An update on the mechanisms of action of the peroxisome proliferator-activated receptors (PPARs) and their roles in inflammation and cancer".

George et al. (2004) Neurobiol Dis 16:124-132 "APP intracellular domain is increased and soluble Aβ is reduced with diet-induced hypercholesterolemia in a transgenic mouse model of Alzheimer disease".

Goodman et al. (editors). (1996). The Pharmacological Basis of Therapeutics, 9.sup.8th Ed., McGraw-Hill. Table of contents.

Grant (1997) Alz. Dis. Rev. 42-55 "Dietary Links to Alzheimer's Disease".

Greenberg et al. (2000) Arch. Neurol. 57:94-99 "Donepezil Theraphy in Clinical Practice: A Randomized Crossover Study".

Gregg et al. (1986) The Journal of Clinical Investigation, Inc. 78:815-821 "Abnormal in Vivo Metabolism of Apolipoprotein E4 in Humans".

Guillot et al. (1993) Brit. J. of Nutri. 69(2):431-42 "Intestinal absorption and liver uptake of medium-chain fatty acids in non-anaesthetized pigs".

Guzman et al. (2001) Trends in Endocrinology Metabolism 12:169-1733 "Is there an astrocyte-neuron ketone body shuttle?"

Haan and Wallace (2004) Annu Rev Public Health 25:1-24 "Can Dementia Be Prevented? Brain Aging in a Population-Based Context".

Halestrap et al. (1999) J. Biol. Chem. 343:281-299 "The proton-linked monocarboxylate transporter (MCT) family: structure, function and regulation".

Hall et al. (1998) Australian and New Zealand Journal of Psychiatry 32:698-706 "Risk factors and Alzheimer's disease: a comparative study of two communities".

Hamosh (1990) Lingual and Gastric Lipases: Their role in fat digestion. CRCpress, Boca Raton, FL pp. 1-34, 114-116, 127-177.

Hanlon et al. (1995) Atherosclerosis 112:85-90 "Arginine residues at codons 112 and 158 in the apolipoprotein E gene correspond to the ancestral state in humans".

Hasselbalch et al. (1996) Am J Physiol 270:E746-751 "Changes in cerebral blood flow and carbohydrate metabolism during acute hyperketonemia".

Hayes (2000) Am. J. Clin. Nutr. 72(6): 1583-1584 "Medium-chain traicylglycerols may not raise cholesterol".

Henderson (2004) Med Hypotheses 62:689-700 "High carbohydrate diets and Alzheimer's disease".

Hertz et al. (2000) Neurochem Int 37(2-3): 83-102 "Neuronal-astrocytic and cystosolic-mitochondrial metabolite trafficking during brain activation, hyperammonemia and energy deprivation".

Ho et al. (2004) Faseb J 18:902-4 "Diet-induced insulin resistance promotes amyloidosis in a transgenic mouse model of Alzheimer's disease".

Hoyer (1992) Mol Chem Neuropathol 16:207-224 "Oxidative Energy Metabolism in Alzheimer Brain".

Hoyer (1998) J. Neural Transm. 105:415-422 "Is sporadic Alzheimer disease the brain type of non-insulin dependent diabetes mellitus? A challenging hypothesis".

Huff et al. (1987) J. Lipid Res. 28:1118-1123 "Separation and isolation of human apolipoproteins C-II, C-IIIo, C-III1, and C-III2 by chromatofocusing on the Fast Protein Liquid Chromatography System".

Jandacek et al. (1978) Chem. Phys. Lipids 22:163-76 "Physical Properties of Pure Sucrose Octaesters".

Johnson et al. (1999) Int J Epidemiol 28:1102-1109 "Adult nutrient intake as a risk factor for Parkinson's disease".

Jolles et al.(1992) Journal of Neurochemistry 58 (6):2326-2329 "Phosphatidylinositol Kinase is Reduced in Alzheimer's Disease".

Jong et al. (1999) Arterioscler. Thromb. Vasc. Biol. 19:472-484 "Role of ApoCs in Lipoprotein Metabolism: Functional Differences Between ApoC1, ApoC2, and ApoC3".

Kalmijn et al. (1997) Ann Neurol 42:776-782 "Dietary Fat Intake and the Risk of Incident Dementia in the Rotterdam Study".

Kashiwaya et al. (2000) Proc. Natl. Acad. Sci. USA 97(10):5440-5444 "D-β-Hydroxybutyrate protects neurons in models of Alzheimer's and Parkinson's disease".

Kimball et al. (2002) J Appl Physiol 93:1168-1680 "Exercise Effects on Muscle Insulin Signaling and Action".

Klivenyi et al. (1999) Nature Medicine 5 (3):347-350 "Neuroprotective effects of creatine in a transfgenic animal model of amyotrophic lateral sclerosis".

Knouff et al. (1999) The Journal of Clinical Investigation 103(11):1579-1586 "Apo E structure determines VLDL clearance and atherosclerosis risk in mice".

Kolanowski et al. (1994) Metabolism 43 (2):180-185 "Stimulatory Influence of D (−) 3-Hydroxybutyrate Feeding on Sympathetic Nervous System Activity in the Rat".

Koo et al. (1999) Proc. Natl. Acad. Sci. 96:9989-9990 "Amyloid diseases: Abnormal protein aggregation in neurodegeneration".

Kudo et al. (1995) J. Biol. Chem. 270:17513-17520 "High Rates of Fatty Acid Oxidation during Reperfusion of Ischemic Hearts Are Associated with a Decrease in Malonyl-CoA Levels Due to an Increase in 5'-AMP-activated Protein Kinase Inhibition of Acetyl-CoA Carboxylase".

Lannert et al. (1998) Behavioral Neuroscience 112 (5):1199-1208 "Intracerebroventricular Administration of Streptozotocin Causes Long-Term Diminutions in Learning and Memory Abilities and in Cerebral Energy Metabolism in Adult Rats".

Lefevre and Aronson (2000) Pediatrics 105:E46 "Ketogenic Diet for the Treatment of Refractory Epilepsy in Children: A Systematic Review of Efficacy".

Leino et al. (2001) Neurochemistry International 38:519-527 "Diet-induced ketosis increases monocarboxylate transporter (MCT1) levels in rat brain".

Ling et al. (2001) J. Med. Chem. 44:3141-3149 "Identification of Alkylidene Hydrazides as Glucagon Receptor Antagonists".

Liu and Barrett (2002) Am J Physiol Endocrinol Metab 283:E1105-1112 "Human protein metabolism: its measurement and regulation".

Loktionov et al. (1999) Atherosclerosis 145:125-135 "Apolipoprotein E and methylenetetrahydrofolate reductase genetic polymiorphisms in relation to other risk factors for cardiovascular disease in UK Caucasians and Black South Africans".

Mahley et al. (1999) J. of Lipid Research 40:1933-49 "Pathogenesis of type III hyperlipoproteinemia (dysbetalipoproteinemia): questions, quandaries, and paradoxes".

Mak et al. (1999) Acta. Paeditr Sin (Medline No. 991412046) 40(2):97-100 "Clinical Experience of Ketogenic Diet on Children With Refractory Epilepsy".

Mattson (1998) Science and Medicine, Mar./Apr.:17-25, Experimental Models of Alzheimer's Disease "Experimental Models of Alzheimer's Disease".

McKhann et al. (1984) Neurology 34:939-943 "Clinical diagnosis of Alzheimer's disease".

Meier-Ruge et al. (1994) Gerontology 40:246-252 "Changes in Brain Glucose Metabolism as a Key to the Pathogenesis of Alzheimer's Disease".

Messier et al. (1996) Behavioural Brain Research 75:1-11 "Glucose regulation and cognitive functions: relation to Alzheimer's disease and diabetes".

Michalik and Van Broeckhoven (2003) Hum Mol Genet 12 Spec No. 2:R173-86 "Pathogenesis of polyglutamine disorders: aggregation revisited".

Mitchell et al. (1995) Clin. Invest. Med. 18:3, 193-216 "Medical aspects of ketone body metabolism".

Moechars et al. (1999) J Biol Chem 274:6483-6492 "Early Phenotypic Changes in Transgenic Mice That Overexpress Different Mutants of Amyloid Precursor Protein in Brain".

Morris et al. (2003) Arch Neurol 60:194-200 "Dietary Fats and the Risk of Incident Alzheimer Disease".

Murray et al. (1999)Harper's Biochemistry 927.

Nadal et al. (2002) Biochem J 366:289-97 "Down-regulation of the mitochondrial 3-hydroxy-3-methylglutaryl-CoA synthase gene by insulin: the role of the forkhead transcription factor FKHRL1".

Nebeling & Lerner (Jun 1995) J. Am. Diet Assoc. 95(6): 693-697 "Implementing a ketogenic diet based on medium-chain triglyceride oil in pediatric patients with cancer".

Neve et al. (1998) Trends Neurosci 21:15-19 "Alzheimer's disease: a re-examination of the amyloid hypothesis".

Nishimura et al. (1999) Clin. Genes 55:219-225 "Biology of presenilins as causative molecules for Alzheimer disease".

Nordberg Lancet Neurol (2004) 3:519-27 "PET imaging of amyloid in Alzheimer's disease".

Odle, J. (1997) J Nutr. 127:1061-1067 "New Insights into the Utilization of Medium-Chain Triglycerides by the Neonate: Observations from a Piglet Model".

Ogawa et al. (1996) J. of the Neurological Sciences 139:78-82 "Altered energy metabolism in Alzheimer's disease".

Osuntokun et al. (1995) Ann Neurol 38:463-465 "Lack of an Association Between Apolipoprotein E E4 and Alzheimer's Disease in Elderly Nigerians".

Pegorier et al. (1988) Biochem Journal 249:801-806, "Fatty acid metabolism in hepatocytes isolates from rats adapted to high-fat diets containing long-or medium-chain triacylglycerols".

Pettegrew et al. (2000) Molecular Psychiatry 5: 616-632 "Acetyl-L-carnitine physical-chemical, metabolic, and therapeutic properties; relevance for its mode of action in Alzheimer's disease and geriatric depression".

Poirier et al. (1995) Proc. Natl. Acad. Sci. 92:12260-12264 "Apolipoprotein E4 allele as a predictor of cholinergic deficits and treatment outcome in Alzheimer disease".

Qureshi et al. (2000) J. Biol. Chem. 275:36590-36595 "Activation of Insulin Signal Transduction Pathway and Anti-diabetic Activity of Small Molecule Insulin Receptor Activators".

Refolo et al. (2000) Neurobiol Dis 7:321-331 "Hypercholesterolemia Accelerates the Alzheimer's Amyloid Pathology in a Transgenic Mouse Model".

Reger (2003) Neurobiol of Aging 25:311 "Effects of β-hydroxybutyrate on cognition in memory-impaired adults".

Reiman et al. (1996) n. Engl J Med 334:752-758 "Preclinical Evidence of Alzheimer's Disease in Persons Homozygous for the E4 Allele for Apolipoprotein E".

Robinson et al. (2004) Neurobiol Aging 25:609-15 "Lessons from the AN 1792 Alzheimer vaccine: lest we forget".

Roheim et al. (1979) Proc Natl Acad Sci U S A 76:4646-4649 "Apoliproteins in human cerebrospinal fluid".

Sato et al. (2003) Exp Biol Med (Maywood) 228:1208-12 "Physical Exercise Improves Glucose Metabolism in Lifestyle-Related Diseases".

Schenk et al. (1999) Nature 400:173-7 "Immunization with amyloid-β attenuates Alzheimerdisease-like pathology in the PDAPP mouse".

Schoonjans et al. (1999) FEBS Lett 452(3): 160-4 "3-Hydroxy-3-methylglutaryl CoA reductase inhibitors reduce serum triglyceride levels through modulation of apolipoprotein C-III and lipoprotein lipase".

Selkoe et al. (1999) Nature 399: A23-31 "Translating cell biology into therapeutic advances in Alzheimer's disease".

Selkoe (2001) Physiol Rev 81(2): 741-66 "Alzheimer's Disease: Genes, Proteins, and Therapy".

Selkoe (2004) Ann Intern Med 140:627-38 "Alzheimer Disease: Mechanistic Understanding Predicts Novel Therapies".

Selkoe, D. J. (1994) J. Neuropathol. Exp. Neurol. 53:438-447 "Alzheimer's Disease: A Central Role for Amyloid".

Shah et al. (2000) Am J Physiol Endocrinol Metab 279:E715-29 "4E-BP1 and S6K15:01 PM translational integration sites for nutritional and hormonal information in muscle".

Shi et al. (1999) J. Biol. Chem. 274: 9421-9426 "A Single Aminio Acid Change (Substitution of Glutamate 3 with Alanine) in the N-terminal Region of Rat Liver Carnitine Palmitoyltransferase I Abolishes Malonyl-CoA Inhibition and High Affinity Binding".

Shie et al. (2002) Neuroreport 13:455-9 "Diet-induced hypercholesterolemia enhances brain a beta accumulation in transgenic mice".

Simpson et al. (1994) Ann Neurol 36:800-801 "Reduced Glucose Transporter Concentrations in Brains of Patients with Alzheimer's Disease".

Sirven, et al. (Dec. 1999) Epilepsia 40(12): 1721-1726 "The Ketogenic Diet for Intractable Epilepsy in Adults: Preliminary Results".

Staels et al. (1998) Circulation 98(19): 2088-93 "Mechanism of Action of Fibrates on Lipid and Lipoprotein Metabolism".

Stokin et al. (2005) Science 307:1282-8 "Axonopathy and Transport Deficits Early in the Pathogenesis of Alzheimer's Disease".

Strittmatter et al. (1996) Annu. Rev. Neurosci. 19:53-77 "Apolipoprotein E and Alzheimer's Disease".

Sugiura et al. (1996) 229:58-64 "2-Arachidonoylglycerol, a Putative Endogenous Cannabinoid Receptor Ligand, Induces Rapid, Transient Elevation of Intracellular Free Ca2+ in Neuroblastoma X Glioma Hybrid NG108-15 Cells".

Sugiura et al. (1997) J. Biol. Chem. 122:890-895 "Is the Cannabinoid CB1 Receptor a 2-Arachidonoylglycerol Receptor? Structural Requirements for Triggering a Ca2+ Transient in NG108-15 Cells".

Sugiura et al. (2000) J. Biol. Chem. 275:605-612 "Evidence That 2-Arachidonoylglycerol but Not N-Palmitoylethanolamine or Anandamide is the Physiological Ligand for the Cannabinoid CB2 Receptor".

Sugiura, et al. (1999) J. Biol. Chem. 274:2794-2801 "Evidence That the Cannabinoid CB1 Receptor Is a 2-Arachidonoylglycerol Receptor".

Swaab et al. (1998) Prog Brain Res 117:343-377 "Reduced neuronal activity and reactivation in Alzheimer's disease".

Takada et al. (1991) Bull. Inst. Chem. Res., 69:77-83 "Preparation of Cellobiose Octa(n-alkanoate)s and Their Thermal Properties".

Takada et al. (1992) Liq. Cryst. 12:337-45 "Columnar liquid crystals in oligosaccharide derivatives".

Takada et al. (1995) Liq. Cryst. 19:441-8 "Discotic columnar liquid crystals in oligosaccharide derivatives".

Taylor et al. (2002) Science 296:1991-5 "Toxic Proteins in Neurodegenerative Disease".

Thal et al. (1996) Neurology 47(3):705-711 "A 1-year multicenter placebo-controlled study of acetyl-L-carnitine in patients with Alzheimer's disease".

Thavendiranathan, et. al. (2000) Exp Neurol 161(2): 696-703 "The MCT Ketogenic Diet: Effects on Animal Seizure Models".

Theodore WH and Gaillard (2002) Prog Brain Res 135: 305-313 "Neuroimaging and the progression of epilepsy".

Van Wymlbeke (2001) Am. J. Clin. Nut. 74:620 "Substrate oxidation and control of food intake in men after a fat-substitute meal compared with meals supplemented with an isoenergetic load of carbohydrate, long-chain triacylglycerols, or medium-chain triacylglycerols".

Veech et al. (2001) IUBMB Life 51(4):241-247 "Ketone Bodies, Potential Therapeutic Uses".

Veneman et al. (1994) Diabetes 43:1311-1317 "Effect of Hyperketonemia and Hyperlacticacidemia on Symptoms, Cognitive Dysfunction, and Counterregulatory Hormone Responses During Hypoglycemia in Normal Humans".

Wang et al. (2005) Faseb J 19:659-661 "Caloric restriction attenuates β-amyloid neuropathology in a mouse model of Alzheimer's disease".

Wang et al. (2000) J. Biol. Chem. 275:20782-20786 "Abnormal Sodium Stimulation of Carnitine Transport in Primary Carnitine Deficiency".

Winocur and Greenwood (1999) Behav Brain Res 101:153-61 "The effects of high fat diets and environmental influences on cognitive performance in rats".

Witters et. al. (1988) Proc. Natl. Acad. Sci. USA 85:5473-5477 "Insulin stimulates the dephosphorylation and activation of acetyl-CoA carboxylase".

Wu et al. (2003) Neuroscience 119:365-75 "A Saturated-Fat Diet Aggravates the Outcome of Traumatic Brain Injury on Hippocampal Plasticity and Cognitive Function by Reducing Brain-Derived Neurotrophic Factor".

Yamamoto et al. 2000 Cell 101:57-66 "Reversal of Neuropathology and Motor Dysfunction in a Conditional Model of Huntington's Disease".

York et al. (1997) Carb. Research 300(3):199-206 "Determination of the absolute configuration of monosaccharides by $^1$H NMR spectroscopy of their per-0-(S)-2-methylbutyrate derivatives".

Zekraoui et al. (1997) Hum Biol 69:575-581 "High frequency of the apolipoprotein E *4 allele in African pygmies and most of the African populations in Sub-Saharan Africa".

Zhao et al. (2004) Pediatr Res 55:498-506 "Detrimental Effects of the Ketogenic Diet on Cognitive Function in Rats".

Zhou et al. (1998) Molecular Endocrinology 12:1594-1604 "Nuclear Receptors Have Distinct Affinities for Coactivators: Characterization by Fluorescence Resonance Energy Transfer".

Zief (1950) J. of Amer. Chem. Soc. 72:1137-40 "Unsaturated esters of sucrose".

Zubenko et al. (1999) Biol Psychiatry 45:731-736 "Reductions in Brain Phosphatidylinositol Kinase Activities in Alzheimer's Disease".

International Search Report, prepared for international patent application PCT/US09/49605 by the U.S. Patent and Trademark Office as International Searching Authority, mailed Aug. 14, 2009, 2 pages.

Extended European Search Report, prepared for European Application No. 07797196.8 by the European Patent Office, dated Aug. 24, 2009, 5 pages.

Birkhahn et al., "Parenteral Monoacetoacetin and Liver Regeneration Interaction After Partial Hepatectomy in the Rat" (1994) Journal of Parenteral and Enteral Nutrition 18(3):219-224 (Abstract Only).

Ko et al., "Bio Salts: Metabolic Pathologic, and Therapeutic Considerations" (1999) Gastroenterology Clinics 28(1):99-115.

USPTO/ISA, "International Search Report" prepared for International Application No. PCT/US09/49609, Sep. 16, 2009, 2 pages.

* cited by examiner

ENZYMATIC SYNTHESIS OF ACETOACETATE ESTERS AND DERIVATIVES

TECHNICAL FIELD

The invention relates to the synthesis of edible acetoacetate esters and derivatives, useful as a source of acetoacetate upon ingestion.

BACKGROUND OF THE INVENTION

In 1979 Birkhahn et al, ((Birkhahn, McMenamy et al. 1979)) described the synthesis of the monoglyceride of acetoacetate which they called monoacetoacetin (MA). The goal was to identify a substrate that would provide a carnitine independent fuel for subjects suffering from sepsis or trauma. The authors listed several reasons for the need for such a compound based on observations of trauma and sepsis patients.

Monoacetoacetin was proposed as a possible compound for parenteral treatment for trauma and sepsis for several reasons, such as that monoacetoacetin is water soluble and does not require emulsification, is metabolized to the safe, naturally occurring compounds of glycerol and acetoacetate, and infusion of monoacetoactin does require a sodium cation, and thus could be administered without increasing sodium load. Direct infusion of ketone bodies would require a sodium cation.

Birkhahn et al. describe the synthesis of MA. MA was synthesized by combining a 1:1 mole ratio of glycerol and diketene and reacted at 80° C. The reaction was stirred for 30 minutes, the product was dissolved in chloroform, washed with water, and separated from solvent under vacuum {Birkhahn, 1978 #412}.

U.S. Pat. No. 5,420,335 entitled "Parenteral nutrients based on water soluble glycerol bisacetoacetates," concerns novel parenteral nutrient compositions consisting of glycerol with two acetoacetates esterified to the OH groups of the glycerol. This patent teaches a method of synthesis of glycerol bisacetoacetate by the method of mixing diketene with glycerol in a solution of dimethylaminopyridine.

U.S. Pat. No. 5,693,850 entitled "Nutritive water soluble glycerol esters of hydroxybutyric acid" was issued Dec. 2, 1997. This patent describes a process for the production of water soluble glycerol esters useful as parenteral nutrients.

U.S. Patent Application Publication No. 2006/0280721 relates to compositions containing (R)-3-hydroxybutyrate derivatives and the use of such compounds for the AD and similar conditions.

The methods of synthesis of described in the prior art require the use of dangerous compounds, such as diketene which is an explosion hazard. Moreover many organic solvents are toxic and therefore organic solvent contamination in pharmaceutical or nutritional products can be a serious problem. Thus it is important to ensure that pharmaceutical and nutritional products are free from solvent contamination, which introduces additional complications and expense.

SUMMARY OF THE INVENTION

The present invention puts forth the novel insight that esters of acetoacetate can be synthesized with the enzymes described herein in a safe and effective manner. In particular the monoacetoacetate of glycerol may be synthesized by this method. Monoacetoacetin represents a therapeutic compound that increases the availability of ketone bodies and to cells of the body, and that this increase in ketone bodies will be beneficial in Alzheimer's disease and other neurodegenerative diseases associated with decreased glucose utilization. Accordingly, the reader sees that the compounds described in this invention can be used to develop treatments and preventative measures for Alzheimer's disease, and other neurodegenerative diseases associated with decreased glucose metabolism. The invention describes methods to synthesize such compounds in an efficient and novel manner.

In one embodiment, the present invention includes a method for the synthesis of an ester derivative of acetoacetate. The method includes providing a first ester of acetoacetate having of formula I:

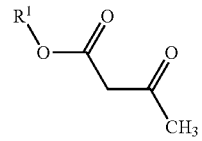

wherein R1 is either an alkyl, alkenyl, alkynyl, halogenated alkyl, cycloalkyl, aliphatic, aryl, or an aralkyl group, and providing an alcohol. The method further includes combining the first ester of acetoacetate and the alcohol in the presence of an enzyme capable of transesterification in a non-aqueous solvent to form the ester derivative of acetoacetate. The method results in the formation of the ester derivative of acetoacetate.

In one embodiment, the ester derivative of acetoacetate is the monoglyceride of acetoacetate. In another embodiment, the first ester of acetoacetate is methylacetoacetate. In another embodiment, the enzyme is a lipase or an esterase.

In one embodiment, the enzyme is selected from the group consisting of *Candida antarctica* lipase, *Aspergillus* lipase, *Thermoanaerobium brockii* esterase, and Esterase E020.

In one embodiment, the non-aqueous solvent is selected from the group consisting of acetonitrile, MTBE, THF, acetone, and toluene. In one embodiment, the non-aqueous solvent is acetonitrile.

In one embodiment, the method further includes purification of the ester derivative of acetoacetate.

In one embodiment, the alcohol is a polyol. In another embodiment, the polyol is glycerol or glucose.

DETAILED DESCRIPTION OF THE INVENTION

The present invention provides convenient and convenient synthesis of esters of acetoacetate can be synthesized with the enzymes described herein in a safe and effective manner. In particular the monoacetoacetate of glycerol (also referred to herein as monoacetoacetin) may be synthesized by this method. The present invention relates to a method of synthesis of acetoacetate derivatives. The method is especially suitable for synthesis of the monoglyceride of acetoacetate but may be used for synthesis of any ester acetoacetate derivative. The compounds synthesized by the method can be used in a variety of therapeutic compositions for which elevation of serum ketone bodies is desired. Examples of such conditions include, sepsis, trauma, neurodegenerative disorders, such as Parkinson's disease and Alzheimer's disease and many others known in the art.

The present invention relates to a simple method for synthesis of any acetoacetate derivatives, preferably monoacetoacetin, which method avoids drawbacks associated with previously described synthesis methods. A preferred acetoacetate derivative produced with the method of the invention is monoacetoacetin. However, the method of the invention is applicable to any acetoacetate derivative, especially for production of nutritive compounds for therapeutic compositions.

In one embodiment, the compounds are used to treat or prevent a variety of disorders in which it is desirable to elevate serum ketone bodies. Preferably, the disorder is Alzheimer's disease or Parkinson's disease.

The present invention includes a method for the synthesis of an ester and/or ester derivative of acetoacetate, comprising providing a first ester of acetoacetate of formula I:

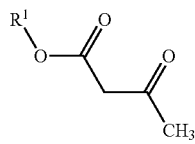

wherein R1 is either an alkyl, alkenyl, alkynyl, halogenated alkyl, cycloalkyl, aliphatic, aryl, or an aralkyl group; providing an alcohol; and combining the first ester of acetoacetate and the alcohol in the presence of an enzyme capable of transesterification in a non-aqueous solvent, wherein said transesterification occurs resulting in an ester and/or ester derivative of acetoacetate. In one embodiment, the enzyme capable of transesterification is capable of transesterifying to the desired product, e.g., an ester derivative of acetoacetate. In another embodiment, the method includes combining the first ester of acetoacetate and the alcohol in the presence of an enzyme capable of transesterification in a non-aqueous solvent to form the ester derivative of acetoacetate. The method results in the formation of the ester derivative of acetoacetate.

In one embodiment, the present invention provides a general method for synthesis of any ketone body derivative, starting with combining an ester of acetoacetate and an alcohol in a non-aqueous environment, comprising the following steps: a) addition of a first ester of acetoacetate and a mono- or polyalcohol to an anhydrous solution; b) addition of a lipase or esterase, and c) purification of reaction product. For production of monoacetoacetin it is preferred to start with methylacetoacetate, glycerol and preferably with *Candida antarctica* lipase. In one embodiment, the reaction step b) is done in the presence of an organic solvent, such as acetonitrile.

"Derivative" refers to a compound or portion of a compound that is derived from or is theoretically derivable from a parent compound.

The term "hydroxyl group" is represented by the formula —OH.

The term "alkoxy group" is represented by the formula —OR, where R can be an alkyl group, including a lower alkyl group, optionally substituted with an alkenyl, alkynyl, aryl, aralkyl, cycloalkyl, halogenated alkyl, or heterocycloalkyl group, as defined below.

The term "ester" is represented by the formula —OC(O)R, where R can be an alkyl, alkenyl, alkynyl, aryl, aralkyl, cycloalkyl, halogenated alkyl, or heterocycloalkyl group, as defined below. "Transesterification" refers to the reaction of an ester with an alcohol to form a new ester compound. In one embodiment, a first ester of acetoacetate, (such as, for example, methyl acetoacetate) is chosen to facilitate formation of the desired new ester (such as, for example, monoacetoacetin).

The term alcohol refers to a broad class of hydroxyl containing organic compounds and includes aliphatic, alicyclic, aromatic, heterocyclic, and polycyclic monohydric alcohols containing one hydroxyl group; aliphatic, alicyclic, aromatic, heterocyclic, and polycyclic dihydric alcohols containing two hydroxyl groups including glycols and diols; aliphatic, alicyclic, aromatic, heterocyclic, and polycyclic trihydric alcohols containing three hydroxyl groups, including glycerol and derivatives, and aliphatic, alicyclic, aromatic, heterocyclic, and polycyclic polyhydric alcohols having three or more hydroxyl groups including saccharides, polysaccharides, and sugar alcohols.

In one embodiment, the alcohol is a polyol. Known polyols are those compounds that include dihydric alcohols having 2 to 20 carbon atoms (aliphatic diols, for instance, alkylene glycols such as ethylene glycol, diethylene glycol, propylene glycol, 1,3- or 1,4-butanediol, 1,6-hexanediol, and neopentylglycol; and alicyclic diols, for instance, cycloalkylene glycols such as cyclohexanediol and cyclohexanedimethanol); trihydric alcohols having 3 to 20 carbon atoms (aliphatic triols, for instance, alkane triols such as glycerol, trimethylolpropane, trimethylolethane, and hexanetriol, and triethanolamine); polyhydric alcohols having 4 to 8 hydroxyl groups and 5 to 20 carbon atoms (aliphatic polyols, for instance, alkane polyols and intramolecular or intermolecular dehydration products of the same such as pentaerythritol, sorbitol, mannitol, sorbitan, diglycerol, and dipentaerythritol; and saccharides and derivatives of the same such as sucrose, glucose, mannose, fructose, and methylglucoside).

Useful polyalcohols for the purposes of the present invention include compounds having at least two hydroxyl (—OH) functions and more preferably at least three, yet more preferably from three to ten, most preferably from three to six and especially from three to four. The polyalcohols can be aliphatic, cycloaliphatic or aromatic, preferably aliphatic or cycloaliphatic and most preferably aliphatic, straight-chain or branched and optionally substituted by functional groups. The polyalcohols generally have from two to 50 and preferably from three to 40 carbon atoms. In one embodiment, although polyhydric alcohols can provide a higher density of acetoacetate equivalents, a polyhydric alcohol will be derivatized at only one hydroxyl group, although derivatization at more than one hydroxyl group is also acceptable.

In one embodiment, polyalcohols are edible polyols such as glycerol or substituted glycerols and saccharides. The edible polyol, in some embodiments, are one or more of the polyols such as carbohydrate alcohols selected from a group consisting of: xylitol, iditol, maltitol, sorbitol, mannitol, dulcitol, inositol, erythritol, lactitol, glycerin, USP glycerin, food grade glycerin, ribitol, threitol, and propylene glycol. The polyol(s) chosen will perform equivalently, limited only by variations of concentrations used and heating and mixing time variations depending upon the polyol, combination of polyols, or polyol solution.

In another embodiment, the alcohol is a saccharide or polysaccharide. The saccharide or polysaccharide can be any known in the art, with an exemplary list including monosaccharides, such as fructose and glucose; disaccharides such as sucrose, maltose, cellobiose, and lactose, or more complex saccharides such as galactose, sorbose, xylose, arinose, and mannose. Additional carbohydrates include altrose, arabinose, dextrose, erythrose, gulose, idose, lyxose, mannose, ribose, talose, threose, and the like.

The term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. In one embodiment, the alkyl group has 1 to 6 carbon atoms. In one embodiment, the alkyl group is methyl.

The term "alkenyl group" is defined as a hydrocarbon group of 2 to 24 carbon atoms and structural formula containing at least one carbon-carbon double bond. In one embodiment, the alkenyl group has 1 to 6 carbon atoms.

The term "alkynyl group" is defined as a hydrocarbon group of 2 to 24 carbon atoms and a structural formula containing at least one carbon-carbon triple bond. In one embodiment, the alkynyl group has 1 to 6 carbon atoms.

The term "halogenated alkyl group" is defined as an alkyl group as defined above with one or more hydrogen atoms present on these groups substituted with a halogen (F, Cl, Br, I).

The term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous. In one embodiment, the cycloalkyl or heterocycloalkyl group has 3 to 10 carbon atoms; in another, 5 to 7 carbon atoms.

The term "aliphatic group" is defined as including alkyl, alkenyl, alkynyl, halogenated alkyl and cycloalkyl groups as defined above. A "lower aliphatic group" is an aliphatic group that contains from 1 to 10 carbon atoms. In one embodiment, the aliphatic group has 1 to 6 carbon atoms.

The term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted. In one embodiment, the aryl group has 3 to 10 carbon atoms; in another, 5 to 7 carbon atoms.

The term "aralkyl" is defined as an aryl group having an alkyl group, as defined above, attached to the aryl group. An example of an aralkyl group is a benzyl group.

"Esterification" refers to the reaction of an alcohol with a carboxylic acid or a carboxylic acid derivative to give an ester. "Transesterification" refers to the reaction of an ester with an alcohol to form a new ester compound.

"Treating" a disease or disorder refers to a therapeutic intervention that ameliorates a sign or symptom of a disease or pathological condition or inhibits the disease from appearing, progressing or developing fully.

The term "3-hydroxybutyrate" is used interchangeably with the term "3-hydroxybutyric acid." The terms "β-hydroxybutyrate" or "β-hydroxybutyric acid" also may be used to refer to this compound.

In one embodiment, the acetoacetate ester formed after transesterification, i.e., the ester derivative of acetoacetate, is the monoglyceride of acetoacetate. In this embodiment, the first, or starting acetoacetate ester is methylacetoacetate. Many other ester derivatives can be formed this way, and include, for example, acetoacetate esters of polyols, saccharides, and sugar alcohols, such as, for example, the acetoacetate ester of glycerol, glucose, sucrose, galactose, mannitol, and 1,3-butandiol. As discussed above, some embodiments include esterification at one hydroxyl, some at two hydroxyls, some at three hydroxyls, some at four hydroxyls, some at five hydroxyls, some at six hydroxyls, some at seven hydroxyls, and more, of the starting alcohol. Exemplary disclosed compounds are described in table 1 below.

TABLE 1

| Alcohol/number of hydroxyls | Acetoacetate residues | Ester bonds |
|---|---|---|
| Glycerol/3 | 3 | 3 |
| Glycerol/3 | 2 | 2 |
| Glycerol/3 | 1 | 1 |
| Glucose/5 | 5 | 5 |
| Glucose/5 | 4 | 4 |
| Glucose/5 | 3 | 3 |
| Glucose/5 | 2 | 2 |
| Glucose/5 | 1 | 1 |
| Galactose/5 | 5 | 5 |
| Galactose/5 | 4 | 4 |
| Galactose/5 | 3 | 3 |
| Galactose/5 | 2 | 2 |
| Galactose/5 | 1 | 1 |
| mannitol/6 | 6 | 6 |
| mannitol/6 | 5 | 5 |
| mannitol/6 | 4 | 4 |
| mannitol/6 | 3 | 3 |
| mannitol/6 | 2 | 2 |
| mannitol/6 | 1 | 1 |
| Sucrose/7 | 7 | 7 |
| Sucrose/7 | 6 | 6 |
| Sucrose/7 | 5 | 5 |
| Sucrose/7 | 4 | 4 |
| Sucrose/7 | 3 | 3 |
| Sucrose/7 | 2 | 2 |
| Sucrose/7 | 1 | 1 |
| 1,3-butanediol/2 | 2 | 2 |
| 1,3-butanediol/2 | 1 | 1 |

In one embodiment the combination is carried out in the presence of an enzyme capable of transesterification to form the desired ester derivative of acetoacetate, such as the monoacetoacetate of glycerol. Many enzymes, such as lipases or esterases, from any number of species, especially bacteria and yeast species, are capable of transesterification. Lipases and esterases catalyze the hydrolysis of ester bonds to produce alcohols and carboxylic acids and have different substrate specificities, R group or chain length preferences, and unique inhibitors. In aqueous solvent systems, esterases and lipases carry out their natural reactions, such as hydrolysis of ester bonds. In organic solvents, where water is excluded, the reactions of esterases and lipases may be reversed and are known to catalyze esterification or acylation reactions to form ester bonds or transesterification.

Such enzymes may be obtained from any of a number of vendors or independently purified using techniques known in the art. In order to determine whether a candidate enzyme, such as a lipase or esterase, is capable of transesterification to form the ester derivative of acetoacetate, one may test a candidate enzyme under appropriate conditions (e.g., with the reactants under the desired reaction conditions) to determine whether the desired transesterified product is formed.

This transesterification step achieves the ester bond between the first ester compound, e.g., a starting ester, most particularly of Formula I, and the hydroxyl group of the alcohol. Any enzyme capable of catalyzing this ester bond reaction is suitable for use. In this reaction advantageously used are enzymes immobilized on an inert organic carrier, which allows them to be easily removed from the reaction medium and then recycled. Preferably, the enzyme will be adsorbed on a macroporous resin.

Surprisingly, many enzymes which are known to have lipase activity fail to achieve the transesterification useful for the present invention. Lipases which fail to achieve the transesterification include lipases derived from *Mucor miehi, Pseudomonas cepacia, Pseudomonoas fluorescens, Rhizopus arrhizus, Candida cylindracea*, Hog pancrease, and *Rhizopus niveus*. Surprisingly, many enzymes which are known to have esterase activity fail to achieve the transesterification useful for the present invention. Esterases which fail to achieve the transesterification include esterases derived from *Bacillus stearothermophilus, Bacillus thermoglucosidasius, Candida lipolytica, Mucor miehei*, horse liver, *Saccharomyces cerevisea*, Hog liver, and THERMOCAT Esterases (also known as E01, E03, E04, E06, E08, E09, E029, N1, N6, N7, N8, N9, N10 and E017b. The THERMOCAT family of esterases is identified in U.S. Pat. No. 6,218,167, U.S. Pat. No. 5,969,121, and U.S. Pat. No. 6,218,163, for example, each of which are incorporated by reference herein in their entireties.

Surprisingly, only a few of the enzymes tested were able to achieve the necessary transesterification, i.e., were capable of forming the ester derivative of acetoacetate. In one embodiment, the enzyme can be any of the following enzymes: *Candida antarctica* lipase B, *Aspergillus* lipase, *Thermoanaerobium brockii* esterase, and THERMOCAT Esterase 20 (E020). Combinations of any of the above-mentioned enzymes are also contemplated. *Candida antarctica* lipase B from any source is suitable for use; in one embodiment, the source is Sigma-Aldrich, *Candida antarctica* lipase B (expressed in *Aspergillus oryzae*) immobilized on an inert support, or such as the product marketed by the firm Novozymes S. A. under the trade name Novozym® 435. This enzyme is thermostable and displays an optimal activity at 40-60° C. It has a declared esterification activity of 10 propyl laurate units per gram. *Aspergillus* lipase is available from, for example, Sigma-Aldrich, provided at approximately 0.5 units/milligram, and has an activity such that 1 U corresponds to the amount of enzyme which hydrolyzes 1 µmol acetic acid per minute at pH 7.4 and 40° C. (triacetin, Fluka No. 90240 as substrate). Esterase from *Thermoanaerobium brockii* from any source is suitable for use; in one embodiment, the source is Sigma-Aldrich, approximately 2 U/g, where a unit is described as the amount of enzyme which hydrolyzes 1 µmol ethyl valerate at 25° C. THERMOCAT 20 is part of a family of esterases dentified in U.S. Pat. No. 6,218,167, U.S. Pat. No. 5,969,121, and U.S. Pat. No. 6,218,163, and is also identified by esterase E020, SEQ ID NOs 29 and 30 in U.S. Pat. No. 6,218,167.

Suitable amounts of enzyme can be determined by one of skill in the art. In one embodiment, approximately one milligram (mg) of each enzyme is used per 2 g methyl acetoacetate and 4 g of glycerol.

The present invention makes use of lipase and/or esterase catalyzed transesterification. Such transesterification can be carried out under any conditions known in the art. Conditions are selected to avoid enzyme catalyzed hydrolysis of the ester starting material to produce acetoacetate. In one embodiment, the reaction is carried out in the presence of at least one non-aqueous solvent. In another embodiment, the reaction is carried out in anhydrous conditions.

Mixing of the ester of Formula I and the alcohol may be performed under a number of stoichiometric ratios. It is noted that a broad range of stoichiometries are functional, such as, for example, between 1:0.1 in terms of units of ester of Formula I:alcohol and between about 1:50 in terms of units of ester of Formula I:alcohol. Exact stoichiometry for a given reaction may be selected by one of skill based on routine experimental activity. In one embodiment, for the synthesis of monoacetoacetin, a ratio of one equivalent of ester of Formula I to three alcohol units may be employed.

The reaction may carried out at a temperature that may comprise the optimum temperature for the enzyme used, but may be carried out at any temperature at which the enzyme operates, with the caveat that temperatures that favor the transesterification reaction and produce more product are preferred. The amount of enzyme to use may also be determined by the skilled person, in accordance with the directive to provide enough enzyme such that the reaction proceeds at an appropriate rate.

The reaction may be carried out under atmospheric pressure or under a reduced pressure or increased pressure.

In order to reach maximum yields of product, the reaction is carried out for at least 8 hours, at least 12 hours, at least 24 hours, at least 48 hours, at least 60 hours, at least 72 hours, at least 84 hours, at least 96 hours, and even greater increments, such as, up to 144 hours.

In one embodiment, the reaction is carried out in at least one organic solvent. In one embodiment, to avoid mass transfer limitations, a solvent that can dissolve the starting materials is desired. For example, to yield monoacetoacetin, solubility of glycerol, methyl acetoacetate, ethyl acetoacetate, and glucose in the solvent is desired. This solvent also should not contain a nucleophile that could compete in the reaction, thus eliminating alcohols. It was found by the present inventors that a non-limiting list of solvents such as acetonitrile, MTBE, THF, acetone, and toluene are suitable for some embodiments of the present invention. For example, glycerol was found to be soluble in THF (>20 g/L), and acetone or acetonitrile (not more than 20 g/L), but only somewhat soluble in MTBE (<10 g/L) and not very soluble in toluene. Glucose was not significantly soluble in acetonitrile, acetone, MTBE, or THF, however, it was partially soluble in toluene (<5 g/L). In one embodiment, the non-aqueous solvent is acetonitrile.

Yields may range from anywhere between about 1% and about 100%. Preferably, the yield is in the range of about 5%, about 10%, about 15%, about 20%, about 30%, about 40%, about 50%, about 60%, about 70%, about 80%, about 90%, about 95%, and about 99%.

The product or ester derivative of acetoacetic acid may be purified from reactants by any known methods. In one embodiment, at the conclusion of the reaction, optionally, the reaction mixture may be filtered, such as through diatomaceous earth such as Celite® or equivalents. Optionally the residue may be washed with a solvent in which the product is not soluble or only sparingly soluble, such as dichloromethane (300 mL). The filtrate may be optionally extracted with aqueous and/or organic phases depending on the relative solubility of the products and reactants. In one embodiment, the filtrate may be concentrated and then re-dissolved in aqueous media such as brine. The aqueous phase may be extracted with a volatile solvent such as ethyl acetate. The organic phase may be optionally dried (such as over sodium sulfate) filtered and/or concentrated.

The method according to the invention offers novel opportunities for the preparation of acetoacetate esters. A specific application is the preparation of nutritive compounds for the treatment of diseases. However, the method is not limited to the production of nutritive compounds but can be used for other purposes.

The invention will now be illustrated with a number of non-limiting patent examples. The invention is defined in more details in the appending claims.

EXAMPLES

Below, the present invention will be described by way of examples, which are provided for illustrative purposes only and accordingly are not to be construed as limiting the scope of the present invention as defined by the appended claims. All references given below and elsewhere in this application are hereby included herein by reference.

Example 1

In order to screen enzymes, appropriate TLC conditions to separate glycerol acetoacetate and starting materials glycerol and ethyl or methyl acetoacetate were used. Silica was developed in 100% isopropyl alcohol and stained with KMnO4 and/or analyzed by UV. Migration was as follows:

| | |
|---|---|
| Methyl acetoacetate (MAA) | Rf ≈ 0.75 |
| Ethyl acetoacetate (EAA) | Rf ≈ 0.75 |
| Glycerol (G) | Rf ≈ 0.5 |
| Glycerol acetoacetate (GAA) | Rf ≈ 0.6 |

Example 2

In order to test lipase and esterase catalyzed transesterification, anhydrous conditions were utilized to avoid enzyme catalyzed hydrolysis of the ester starting material to produce acetoacetate. In evaluating organic solvents with which to carry out the reaction, it is important to avoid mass transfer limitations by use of a solvent that dissolves glycerol, methyl acetoacetate, ethyl acetoacetate, and glucose. This solvent also should not contain a nucleophile that could compete in the reaction, thus eliminating alcohols. Acetonitrile, MTBE, THF, acetone, and toluene were tested for ability to dissolve the substrates. The acetoacetate esters were very soluble in all solvents tested. Glycerol was soluble in THF (>20 g/L), and acetone or acetonitrile (not more than 20 g/L), but only somewhat soluble in MTBE (<10 g/L) and not very soluble in toluene. Glucose was not significantly soluble in acetonitrile, acetone, MTBE, or THF, however, it was partially soluble in toluene (<5 g/L).

Activity of Enzymes in Organic Solvents:

Based on the solubility data, acetonitrile and THF were selected for analysis of enzyme activity. In order to decide which solvent to use in the screening, enzyme activity of the partial library of esterases and lipases (Table 1) was tested using colorimetric reagent 4-nitrophenyl butyrate. A solution of 1% 4-nitrophenyl butyrate was prepared in THF and acetonitrile (each containing 1% water to promote hydrolysis) and 50 μL aliquots were incubated @ RT with 1-2 mg of 10 randomly selected enzymes. After 2 hr, 50 μL of pH 9.0 Tris was added to the reactions and the developed yellow color due to released para-nitrophenol was compared. The general trend was that all enzymes displayed hydrolysis under the reaction conditions, but in acetonitrile the reactions generally proceeded to a greater extent as visualized by a more intense yellow color.

Example 3

Glycerol Enzyme Screening

In order to determine which enzymes are useful for synthesis of monoacetoacetin, glycerol 4 g was mixed with methyl acetoacetate 2 g and dissolved in 150 mL acetonitrile to which 50 mL of MTBE was added and subsequently evaporated under vacuum to remove residual water in the acetonitrile and glycerol. The final volume of the mixture was 100 mL. After removal of the water, some (~0.5 g) glycerol came out of solution, but most remained dissolved. Approximately 1 mg of each enzyme was placed in a 0.5 mL polypropylene tube and 100 μL of the prepared substrate mix was added to each tube, vortexed, and then incubated @ 37° C. on a rotary shaker @ 200 rpms.

At 24 hours the samples were analyzed by TLC. The positive controls are marked with black circles, yellow arrows point to positive hits. Enzyme #12 (*Candida antarctica* lipase) produced a significant amount of product with the same Rf as the standard glycerol acetoacetate.

After 96 hours of incubation several other enzymes were able to produce detectable amounts of product with Rf values consistent with GAA. These enzymes are esterase *Thermoanaerobium brockii*, Lipase *Aspergillus*, and ThermoCat Esterase #20.

Example 4

Glucose Enzyme Screening

Anhydrous glucose 8 mg is placed in 0.5 mL tubes (40) along with 1-2 mg of each enzyme. In 33 mL anhydrous acetonitrile, 0.825 mls (0.2 mol) methyl acetoacetate is added, from which 100 μL is added to each tube containing enzyme and glucose. The tubes are subsequently incubated at 37° C. and 200 rpms. Samples are analyzed by TLC at 24, 72, and 144 hrs. It is found that one or more enzymes would produce the glucose acetoacetate ester, including (*Candida antarctica* lipase), Esterase *Thermoanaerobium brockii*, Lipase *Aspergillus*, and ThermoCat Esterase #20.

Example 5

Synthesis of Monoacetoacetin

Synthesis of monoacetoacetin was accomplished by the general scheme of combining glycerol, methylacetoacetate and a lipase in an anhydrous environment as outlined below

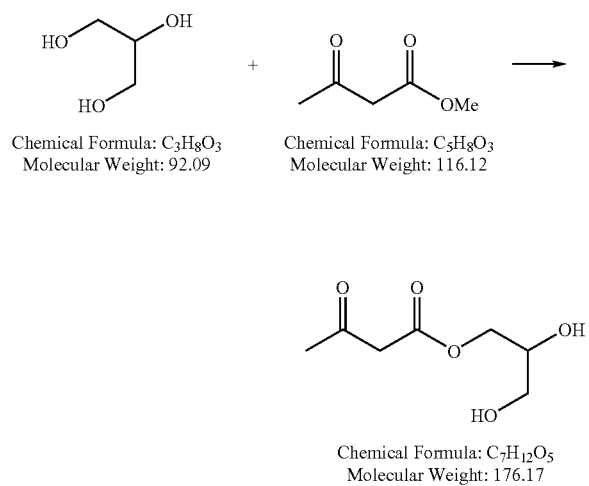

Chemical Formula: $C_3H_8O_3$
Molecular Weight: 92.09

Chemical Formula: $C_5H_8O_3$
Molecular Weight: 116.12

Chemical Formula: $C_7H_{12}O_5$
Molecular Weight: 176.17

| Reactant | Mol. Wt. | Equiv. | Mass (g) | Density (g/mL) | Volume (mL) | Scale (mmol) |
|---|---|---|---|---|---|---|
| Methyl Acetoacetate | 116.12 | 1 | 4.3 | 1.076 | 3.996283 | 37.03065794 |
| Glycerol | 92.09 | 2.95 | 10.0599522 | 1.262 | 7.971436 | 109.2404409 |
| Lipase Acrylic Resin (*Candida antarctica* Lipase B) | NA | NA | 2 | | | NA |

| Solvent 1 | Amount (mL) | Solvent 2 | Amount (mL) | Solvent 3 | Amount (mL) | Rxn Conc. (M) |
|---|---|---|---|---|---|---|
| Acetonitrile | 100 | Unspecified | 0 | Unspecified | 0 | 0.370306579 |

Glycerol, obtained from Sigma-Aldrich (10.05 g, 109.2 mmol) is weighed into a 250 mL round bottomed flask and co-evaporated with acetonitrile (2×50 mL). Methyl acetoacetate (4.30 g, 37.03 mmol), was obtained from Sigma-Aldrich. *Candida antarctica* Lipase B (2.00 g) (obtained from Sigma-Aldrich) and a stir bar are added to the flask, which is septum sealed and flushed with argon. The flask is charged with acetonitrile (100 mL) and allowed to stir, under argon at 40° C. for 5 days. The reaction mixture was filtered through Celite® and the residue was washed with dichloromethane (300 mL). The filtrate was concentrated and re-dissolved in brine (100 mL). The aqueous phase was extracted with ethyl acetate (3×100 mL). The organic phase was combined, dried over sodium sulfate, filtered and concentrated to give 2.30 g (35.3%) of a clear and colorless oil. TLC reveals the presence of a single product (TLC, 40% acetone in hexanes, PMA visualization).

What is claimed is:

1. A method for the synthesis of an ester derivative of acetoacetate, comprising providing a first ester of acetoacetate having of formula I:

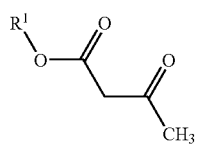

wherein R1 is either an alkyl, alkenyl, alkynyl, halogenated alkyl, cycloalkyl, aliphatic, aryl, or an aralkyl group;

providing a compound selected from the group consisting of glucose and glycerol; and combining the first ester of acetoacetate and the compound in the presence of an enzyme capable of transesterification selected from the group consisting of esterase *Thermoanaerobium brockii*, and Esterase 20 (E020) in a non-aqueous solvent selected from the group consisting of acetonitrile, methyl tertiary butyl ester (MTBE), tetrahydrofuran (THF), acetone, and toluene thereby forming the ester derivative of acetoacetate.

2. The method of claim 1, wherein the compound is glycerol and the ester derivative of acetoacetate is monoglyceride of acetoacetate.

3. The method of claim 1, wherein the compound is glucose and the first ester of acetoacetate is glucose acetyl acetate ester.

4. The method of claim 1, wherein the non-aqueous solvent is acetonitrile.

5. The method of claim 1, further comprising purification of the ester derivative of acetoacetate.

* * * * *